United States Patent [19]

Ozaki et al.

[11] Patent Number: 5,380,944
[45] Date of Patent: Jan. 10, 1995

[54] BENZHYDRAZONE DERIVATIVES AS AN INTERMEDIATE FOR THE PRODUCTION OF TRIAZOLE DERIVATIVES

[75] Inventors: Masami Ozaki; Reijiro Honami; Takashi Yumita; Atsuhiko Ikeda, all of Iwata; Naokazu Minoguchi; Norihiko Izawa, both of Ogasa; Tadayoshi Hirano, Kakegawa, all of Japan

[73] Assignees: Kumiai Chemical Industry Co., Ltd.; Ihara Chemical Industry Co., Ltd., both of Tokyo, Japan

[21] Appl. No.: 141,876

[22] Filed: Oct. 27, 1993

Related U.S. Application Data

[63] Continuation-in-part of Ser. No. 956,980, Oct. 6, 1992, Pat. No. 5,284,860.

[30] Foreign Application Priority Data

Mar. 4, 1992 [JP] Japan .................................. 4-81412

[51] Int. Cl.⁶ .......................................... C07C 311/49
[52] U.S. Cl. ...................................... 564/81
[58] Field of Search ................ 564/81, 102; 546/276; 514/340

[56] References Cited

U.S. PATENT DOCUMENTS 4,414,221 11/1983 Parsons et al. .................. 514/383
4,788,210 11/1988 Lüthy et al. ..................... 514/383
4,954,503 9/1990 Strupczewski et al. ......... 514/254

FOREIGN PATENT DOCUMENTS 185256  6/1986 European Pat. Off. .
0217552 4/1987 European Pat. Off. .
3631511 9/1986 Germany .

OTHER PUBLICATIONS

Ito et al. "N-phenylsulfonyl and N-methyl-N-phenylsulfonyl benzohydrazonoyl Azides" Bull. Chem. Soc. Jpn. 57 539-543 (1984).

Research Disclosure, vol. 278, Jun. 1987, pp. 356-357.

Primary Examiner—Celia Chang
Attorney, Agent, or Firm—Stevens, Davis, Miller & Mosher

[57] ABSTRACT

A novel benzhydrazone derivative has a general formula [I]:

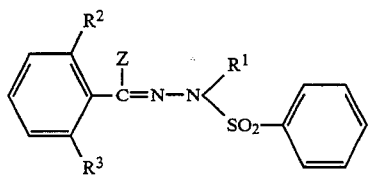

(wherein $R^1$ is a lower alkyl group, $R^2$ and $R^3$ are same or different halogen atoms and Z is a chlorine atom or an amino group) and is useful as an intermediate for the production of a triazole derivative having the following general formula [II]:

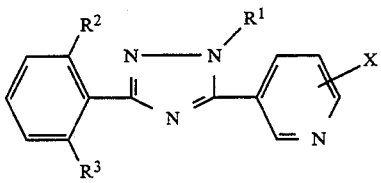

(wherein $R^1$, $R^2$ and $R^3$ are the same as mentioned above and X is a chlorine atom located at 2- or 6-position).

3 Claims, No Drawings

BENZHYDRAZONE DERIVATIVES AS AN INTERMEDIATE FOR THE PRODUCTION OF TRIAZOLE DERIVATIVES

This application is a continuation-in-part of the co-pending application Ser. No. 07/956,980 filed Oct. 6, 1992 and now allowed U.S. Pat. No. 5,284,860.

BACKGROUND OF THE INVENTION

1. Field of the Invention

This invention relates to a novel benzhydrazone derivative as an intermediate for the production of triazole derivatives useful as an insecticide.

2. Description of the Related Art

It is known that triazole derivatives such as 3-(2-chlorophenyl)-5-(6-chloropyridin-3-yl)-1-methyl-1H-1,2,4-triazole and the like are effective for the control of mites and sap-sucking insects (Research Disclosure RD278004). In this literature, however, there is no description that what concentration of the above derivative is effective to what kind of injurious insect and also the origin for these derivatives is unclear. Further, the compounds concretely described in the above literature are poor in the systemic trans-location and the systemic penetrance and are hardly said to be satisfactory as an insecticide.

As an injurious insect harming farm and garden products, there are aphids such as cotton aphid, green peach aphid, foxglove aphid and the like. These aphids eat growing points of plants to badly damage farm and garden products and also they infect virus. Therefore, it is strongly demanded to control these aphids. Lately, injurious insects developing resistance to existing insecticide and acaricide appear and the control thereof becomes more serious. In this connection, chemicals for controlling hemiptera insects typified by aphids are desirable to have systemic translocation and systemic penetrance as a functional performance.

SUMMARY OF THE INVENTION

The inventors nave synthesized various triazole derivatives in order to develop an insecticide useful for the control of the above injurious insects and made studies with respect to their physiological activities, during which many benzhydrazone derivatives have been synthesized as an intermediate for the production of the triazole derivative.

As a result, the inventors have found that benzhydrazone derivatives having a general formula [I] as mentioned later are novel and suitable as an intermediate for the triazole derivative.

According to the invention, there is the provision of a novel benzhydrazone derivative having the following general formula [I]:

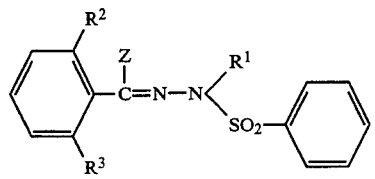

(wherein $R^1$ is a lower alkyl group, $R^2$ and $R^3$ are same or different halogen atoms and Z is a chlorine atom or an amino group).

DESCRIPTION OF THE PREFERRED EMBODIMENTS

The benzhydrazone derivatives of the formula [I] according to the invention are shown in Table 1, in which the compound No. is referred in subsequent description.

TABLE 1

![formula structure with $R^2$, $R^3$, Z, $R^1$, C=N-N, SO_2]

| Compound No. | $R^1$ | $R^2$ | $R^3$ | X | Physical properties melting point (°C.) or refractive index ($n_D^{20}$) |
|---|---|---|---|---|---|
| 1 | CH$_3$ | F | F | Cl | 81.5~83.0 |
| 2 | CH$_3$ | Cl | F | Cl | 103.0~105.0 |
| 3 | CH$_3$ | Cl | Cl | Cl | 106.0~108.0 |
| 4 | CH$_3$ | F | F | NH$_2$ | 68.0~74.0 |
| 5 | CH$_3$ | Cl | F | NH$_2$ | 76.0~80.0 |
| 6 | CH$_3$ | Cl | Cl | NH$_2$ | not measurable |

The benzhydrazone derivative according to the invention is usable as an intermediate for the production of a triazole derivative having the following general formula [II]:

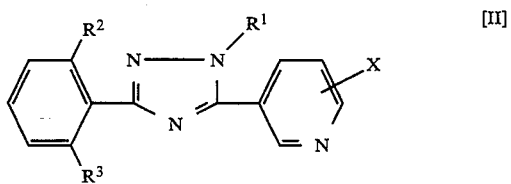

(wherein $R^1$, $R^2$ and $R^3$ are the same as mentioned above and X is a chlorine atom located at 2- or 6-position).

The triazole derivatives of the general formula [II] are shown in Table 2, in which the compound No. is referred in subsequent description.

TABLE 2

| Compound No. | $R^1$ | $R^2$ | $R^3$ | X | Physical properties melting point (°C.) or refractive index ($n_D^{20}$) |
|---|---|---|---|---|---|
| 7 | CH$_3$ | F | F | 2-Cl | 167.0~171.0 |
| 8 | CH$_3$ | F | Cl | 2-Cl | 48.0~52.0 |
| 9 | CH$_3$ | Cl | Cl | 2-Cl | 133.0~135.5 |
| 10 | C$_2$H$_5$ | F | Cl | 2-Cl | 101.0~103.0 |
| 11 | C$_3$H$_7$-i | F | Cl | 2-Cl | 156.0~160.0 |
| 12 | CH$_3$ | F | F | 6-Cl | 138.0~141.0 |
| 13 | CH$_3$ | F | Cl | 6-Cl | 118.5~120.5 |
| 14 | CH$_3$ | Cl | Cl | 6-Cl | 167.0~171.0 |
| 15 | CH$_3$ | F | I | 6-Cl | 40.0~42.0 |
| 16 | C$_2$H$_5$ | F | Cl | 6-Cl | 102.0~105.0 |
| 17 | C$_3$H$_7$-i | F | Cl | 6-Cl | not measurable |

The benzhydrazone derivatives according to the invention can be produced according to the following methods, but it is not intended to restrict these methods.

Firstly, 1-benzoyl-2-phenylsulfonyl hydrazine derivative [IV] as a starting material can be obtained by reacting a halogenated benzoyl derivative represented by the general formula [III] with benzene sulfonyl hydrazide in an inert solvent in the presence of a base according to the following reaction formula:

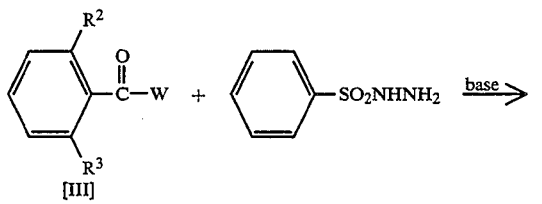

(wherein W is a halogen atom and $R^2$ and $R^3$ are the same as mentioned above).

As the inert solvent, use may be made of any solvents not obstructing the reaction, which include an ether such as diethyl ether, tetrahydrofuran, dioxane, diglyme or the like; an aliphatic hydrocarbon such as pentane, hexane or the like; an aromatic hydrocarbon such as benzene, toluene or the like; a halogenated hydrocarbon such as dichloromethane, chloroform, carbon tetrachloride, dichloroethane, chlorobenzene, dichlorobenzene or the like; dimethylformamide, dimethylacetamide, dimethylsulfoxide, N-methyl pyrrolidone, and a mixture thereof.

As the base, use may be made of an inorganic base such as potassium carbonate, sodium carbonate, sodium hydrogencarbonate, potassium hydroxide, sodium hydroxide, potassium hydride, sodium hydride or the like; and an organic base such as trimethylamine, diethylamine, triethylamine, pyridine, 4-N,N-dimethyl aminopyridine or the like.

The amounts of benzene sulfonylhydrazide and the base used are usually 1.0–1.5 mole and 1.0–2.0 mole per 1 mole of the halogenated benzoyl derivative [III], respectively. The reaction temperature is dependent upon the kind of the compound used, but is within a range of from $-10°$ C. to a boiling point of the solvent used. The reaction time is usually within a range of 1–48 hours.

Secondly, 1-benzoyl-2-alkyl-2-phenyl sulfonylhydrazine derivative [VI] as a starting material can be produced by reacting 1-benzoyl-2-phenyl sulfonylhydrazine derivative of the general formula [IV] with a halogenated alkyl derivative represented by the general formula [V] in an inert solvent in the presence of a base according to the following reaction formula:

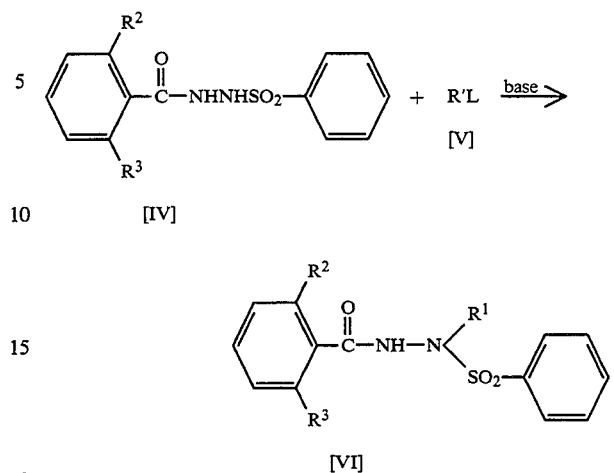

(wherein $R^1$, $R^2$ and $R^3$ are the same as mentioned above).

As the inert solvent, use may be made of any solvents not obstructing the reaction, which include an ether such as diethyl ether, tetrahydrofuran, dioxane, diglyme or the like; an aliphatic hydrocarbon such as pentane, hexane or the like; an aromatic hydrocarbon such as benzene, toluene, xylene or the like; a halogenated hydrocarbon such as dichloromethane, chloroform, carbon tetrachloride, dichloroethane, chlorobenzene, dichlorobenzene or the like; dimethylformamide, dimethylacetamide, dimethylsulfoxide, N-methyl pyrrolidone, and a mixture thereof.

As the base, use may be made of an inorganic base such as potassium carbonate, sodium carbonate, sodium hydrogencarbonate, potassium hydroxide, sodium hydroxide, potassium hydride, sodium hydride or the like; and an organic base such as potassium tertbutoxide, n-butyllithium or the like.

The amounts of the halogenated alkyl derivative [V] and the base used are usually 1.0–2.0 mole and 1.0–2.0 mole per 1 mole of 1-benzoyl-2-phenyl sulfonylhydrazine derivative [IV], respectively. The reaction temperature is dependent upon the base and halogenated alkyl agent used, but is within a range of from $-30°$ C. to a boiling point of the solvent used. The reaction time is usually within a range of 1–48 hours.

Then, N-alkyl-N-(phenylsulfonyl)-benzhydrazonoyl chloride derivative represented by the general formula [VII] can be produced by reacting 1-benzoyl-2-alkyl-2-phenyl sulfonylhydrazine derivative [VI] with a chlorinating agent in a solvent.

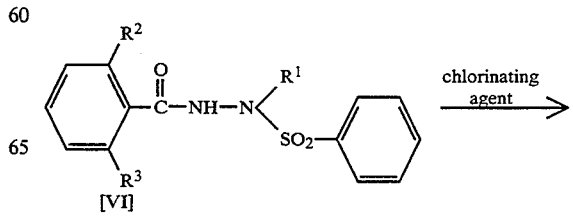

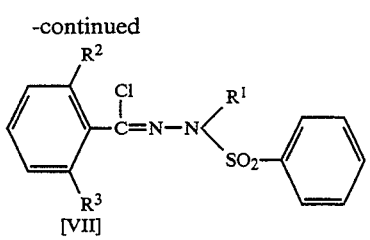

As the chlorinating agent, use may be made of thionyl chloride, phosphorus oxychloride, phosphorus pentachloride, carbon tetrachloride, triphenylphosphine and the like. If necessary, a mixture of phosphorus pentachloride and phosphorus oxychloride can be used. In the latter case, an excessive amount of phosphorus oxychloride acts as a solvent. As the solvent, use may be made of an aliphatic hydrocarbon such as pentane, hexane or the like; an aromatic hydrocarbon such as benzene, toluene, xylene or the like; and a halogenated hydrocarbon such as dichloroethane, chloroform, carbon tetrachloride, chlorobenzene, dichlorobenzene or the like.

The amount of the chlorinating agent used is usually 1.0–10.0 mole per 1 mole of 1-benzoyl-2-alkyl-2-phenyl sulfonylhydrazine derivative [VI].

The reaction temperature is optional within a range of from 0° C. to a boiling point of the solvent used, but is preferably within a range of 50°–120° C.

On the other hand, N-(phenylsulfonyl) benzamidrazone derivative represented by the general formula [VII] can be produced by reacting N-(phenylsulfonyl) benzhydrazonoyl chloride derivative of the general formula [VII] with ammonia gas in an inert solvent according to the following reaction formula:

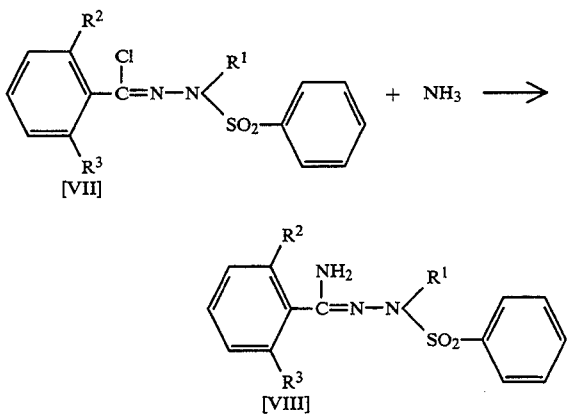

(wherein $R^1$, $R^2$ and $R^3$ are the same as mentioned above).

As the inert solvent, use may be made of any solvents not obstructing the reaction, which include an ether such as diethyl ether, tetrahydrofuran, dioxane, diglyme or the like; an aromatic hydrocarbon such as benzene, toluene, chlorobenzene, or the like; an aliphatic hydrocarbon such as pentane, hexane, petroleum ether or the like; a halogenated hydrocarbon such as dichloromethane, dichloroethane, chloroform, carbon tetrachloride, or the like; dimethylformamide, dimethylacetamide, dimethylsulfoxide or a mixture thereof. In general, the ammonia gas is used in an amount of 5.0–10.0 mole per 1 mole of N-(phenylsulfonyl) benzhydrazonoyl chloride derivative [VII].

The reaction temperature is optional within a range of from 0° C. to a boiling point of the solvent used, but is preferably within a range of 50°–150° C. The reaction time is dependent upon the starting compounds used, but is usually within a range of 5–20 hours.

The triazole derivatives of the general formula [II] can be produced by the following methods using the above benzhydrazone derivative as an intermediate.

That is, the compound of the general formula [II] can be obtained by reacting N-(phenylsulfonyl) benzhydrazonoyl chloride derivative [VII] with 3-cyanopyridine derivative of the general formula [IX] in an inert solvent in the presence of Lewis acid according to the following reaction formula:

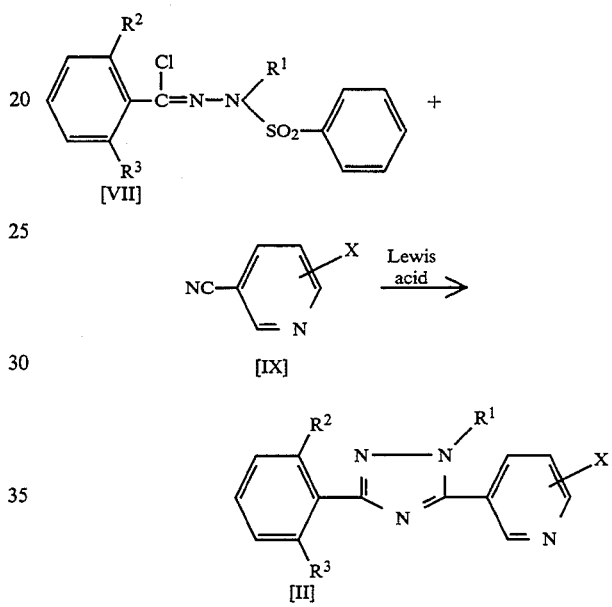

(wherein $R^1$, $R^2$, $R^3$ and X are the same as mentioned above).

As the inert solvent, use may be made of any solvents not obstructing the reaction, which include an ether such as diethyl ether, tetrahydrofuran, dioxane, diglyme or the like; an aromatic hydrocarbon such as benzene, toluene, chlorobenzene, dichlorobenzene or the like; an aliphatic hydrocarbon such as pentane, hexane, petroleum ether or the like; a halogenated hydrocarbon such as dichloromethane, dichloroethane, chloroform, carbon tetrachloride or the like; dimethylformamide, dimethylacetamide, dimethylsulfoxide or a mixture thereof. In general, 3-cyanopyridine derivative [IX] and Lewis acid are used in an amount of 1.0–2.0 mole per 1 mole of N-(phenylsulfonyl) benzhydrazonoyl chloride derivative [IV], respectively.

The reaction temperature is optional within a range of from 0° C. to a boiling point of the solvent used, but is preferably within a range of 50°–150° C. The reaction time is dependent upon the starting compounds used, but is usually within a range of 30 minutes to 5 hours.

Alternatively, the compound of the general formula [II] can be obtained by reacting N-(phenylsulfonyl) benzamidrazone derivative of the general formula [VII] with the nicotinoylhalide derivative of the general formula [X] in an inert solvent according to the following reaction formula:

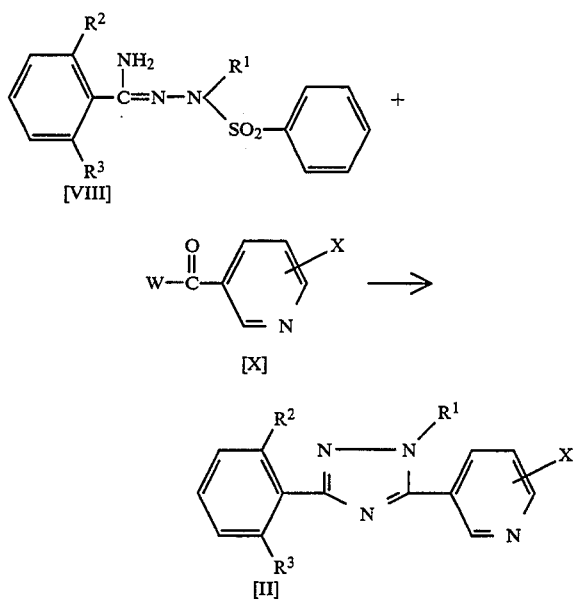

(wherein $R^1$, $R^2$, $R^3$, W and X are the same as mentioned above).

As the inert solvent, use may be made of any solvents not obstructing the reaction, which include an ether such as diethyl ether, tetrahydrofuran, dioxane, diglyme or the like; an aromatic hydrocarbon such as benzene, toluene, chlorobenzene or the like; an aliphatic hydrocarbon such as pentane, hexane, petroleum ether or the like; a halogenated hydrocarbon such as dichloromethane, dichloroethane, chloroform, carbon tetrachloride or the like; dimethylformamide, dimethylacetamide, dimethylsulfoxide or a mixture thereof. In general, the nicotinoylhalide derivative [X] is used in an amount of 1.0–2.0 mole per 1 mole of N-(phenylsulfonyl) benzamidrazone derivative [VIII].

The reaction temperature is optional within a range of from 0° C. to a boiling point of the solvent used, but is preferably within a range of 50°–200° C. The reaction time is dependent upon the starting compounds used, but is usually within a range of 30 minutes to 5 hours.

The following examples are given in illustration of the invention and are not intended as limitations thereof.

EXAMPLE 1

Production of
N-methyl-N-phenylsulfonyl-2,6-difluorobenzhydrazonoyl Chloride (Compound No. 1)

In 800 ml of tetrahydrofuran are dissolved 125.0 g of benzene sulfonylhydrazide and 76.0 g of triethylamine, to which is added dropwise 129.0 g of 2,6-difluorobenzoyl chloride within a temperature range of 0°–10° C. with stirring. The resulting mixture is further stirred at room temperature for 6 hours. After the completion of the reaction, the solvent is distilled off under a reduced pressure and the residue is extracted with 800 ml of ethyl acetate. The extract is washed with water and dried over anhydrous sodium sulfate and then the solvent is distilled off under a reduced pressure.

The resulting crude crystal is dissolved in 1000 ml of dimethylformamide, to which is added 21.5 g of 60% sodium hydride within a temperature range of 5°–20° C. over 30 minutes with stirring. The resulting mixture is further stirred at 5°–10° C. for 1 hour. After 79.0 g of methyl iodide is added dropwise at 5°–10° C., the stirring is continued at room temperature for 20 hours. After the completion of the reaction, the reaction product is added with water and extracted with 1400 ml of ethyl acetate. The extract is washed with water and dried over anhydrous sodium sulfate and then the solvent is distilled off under a reduced pressure.

The thus purified crystal is mixed with 240 g of thionyl chloride and refluxed by heating for 16 hours and then an excessive amount of thionyl chloride is distilled off under a reduced pressure. The residue is added with water and extracted with 800 ml of ethyl acetate. The extract is washed with water and dried over anhydrous sodium sulfate and the solvent is distilled off under a reduced pressure. The resulting oily substance is crystallized by adding a mixed solvent of n-hexane/ethanol (50:50) to obtain 84.5 g of a desired colorless prism crystal (melting point: 81.5°–83.0° C.).

EXAMPLE 2

Production of
N-methyl-N-phenylsulfonyl-2,6-difluorobenzamidrazone (Compound No. 4)

In 300 ml of! dimethylformamide is dissolved 34.5 g of N-methyl-N-phenylsulfonyl--2,6-difluorobenzhydrazonoyl chloride, which is reacted by blowing ammonia gas at 80°–100° C. for 16 hours with stirring. After the completion of the reaction, the resulting mixture is added with water and extracted with 500 ml of ethyl acetate. The extract is washed with water and dried over anhydrous sodium sulfate and the solvent is distilled off under a reduced pressure. The resulting crude crystal is washed with a mixed solvent of n-hexane/ethanol (50:50) to obtain 15.5 g of a desired colorless granular crystal (melting point: 68.0°–74.0° C.).

EXAMPLE 3

Production of
N-methyl-N-phenylsulfonyl-2-chloro-6-fluorobenzhydrazonoyl Chloride (Compound No. 2)

In 700 ml of tetrahydrofuran are dissolved 103.3 g of benzene sulfonylhydrazide and 66.0 g of triethylamine, to which is added dropwise 115.8 g of 2-chloro-6-fluorobenzoyl chloride within a temperature range of −5° C. to 5° C. with stirring. The resulting mixture is further stirred at room temperature for 6 hours. After the completion of the reaction, the solvent is distilled off under a reduced pressure and the residue is extracted with 1000 ml of ethyl acetate. The extract is washed with water and dried over anhydrous sodium sulfate and the solvent is distilled off under a reduced pressure.

The resulting crude crystal is dissolved in 1000 ml of dimethylformamide, to which is added 17.0 g of 60% sodium hydride within a temperature range of 5°–20° C. over 20 minutes with stirring. The resulting mixture is stirred at 5°–10° C. for 1 hour. After 60.0 g of methyl iodide is added dropwise at 5°–10° C., the stirring is continued at room temperature for 20 hours. After the completion of the reaction, the reaction mixture is added with water and extracted with 1400 ml of ethyl acetate. The extract is washed with water and dried over anhydrous sodium sulfate and the solvent is distilled off under a reduced pressure.

The thus purified crystal is mixed with 400 g of thionyl chloride and refluxed by heating for 16 hours and then an excess amount of thionyl chloride is distilled off under a reduced pressure. The resulting oily substance is crystallized by adding a mixed solvent of n-hexane/ethanol (50:50) to obtain 88.9 g of a desired colorless granular crystal (melting point: 103.0°–105° C.).

EXAMPLE 4
Production of N-methyl-N-phenylsulfonyl-2-chloro-6-fluorobenzamidrazone (Compound No. 5)

In 300 ml of dimethylformamide is dissolved 36.1 g of N-methyl-N-phenylsulfonyl-2-chloro-6-fluorobenzhydrazonoyl chloride, which is reacted by blowing ammonia gas at 80°–100° C. for 16 hours with stirring. After the completion of the reaction, the resulting mixture is added with water and extracted with 500 ml of ethyl acetate. The extract is washed with water and dried over anhydrous sodium sulfate and the solvent is distilled off under a reduced pressure. The resulting crude crystal is washed with a mixed solvent of n-hexane/ethanol (50:50) to obtain 19.5 g of a desired colorless granular crystal (melting point: 76.0°–80.0° C.).

Reference Example 1
3-(2,6-dichlorophenyl)-5-(2-chloropyridin-3-yl)-1-methyl-1H-1,2,4-triazole (Compound No. 9)

In 50 ml of dichlorobenzene were dissolved 5.7 g of N-methyl-N-phenylsulfonyl-2,6-dichloro-benzohydrazonoyl chloride and 2.3 g of 2-chloro-3-cyanopyridine, to which was added 2.2 g of anhydrous aluminum chloride at room temperature with stirring. The resulting solution was raised to 120°–140° C. in an oil bath and stirred for 4 hours. After the completion of the reaction, the reaction solution was washed with a diluted alkali solution and further with a diluted hydrochloric acid solution. After the washing with water, the organic layer was dried over anhydrous magnesium sulfate and concentrated under a reduced pressure. The resulting concentrate was subjected to a chromatography of silica gel (trade mark: Wakogel C-200) using a mixed solution of hexane and ethyl acetate as a developing solvent to obtain 1.9 g (yield: 37.3%) of a desired light brown granular crystal (melting point: 133.0°–135.5° C.).

NMR data (60 MHz, CDCl$_3$ solvent, δ value) 3.93 (s, 3H) 7.30–7.63 (m, 4H) 7.95 (dd, 1H) 8.55 (dd, 1H)

Reference Example 2
3-(2-chloro-6-fluorophenyl)-5-(6-chloropyridin-3-yl)-1-methyl-1H-1,2,4-triazole (Compound No. 13)

In 50 ml of 1-methyl-2-pyrrolidone (NMP) were dissolved 8-8 g of N-methyl-N-phenylsulfonyl-2-chloro-6-fluorobenzamidrazone and 4.5 g of 6-chloronicotynoyl chloride. The resulting solution was raised to 110°–120° C. in an oil bath and stirred for 2 hours. It was further raised to 170°–180° C. and stirred for 4 hours. After the completion of the reaction, it was added with 200 ml of chloroform and washed with water. The resulting organic layer was dried over anhydrous magnesium sulfate and concentrated under a reduced pressure. The resulting concentrate was subjected to a chromatography of silica gel (trade mark: Wakogel C-200) using a mixed solution of hexane and ethyl acetate as a developing solvent to obtain 2.0 g (yield: 35.5%) of a desired yellow granular crystal (melting point: 118.5°–120.5° C.).

NMR data (60 MHz, CDCl$_3$ solvent, δ value) 4.03(s, 3H) 6.83–7.50 (m, 4H 8.05(dd, 1H) 8.75(dd, 1H)

Reference Example 3
3-(2-chloro-6-fluorophenyl)-5-(6-chloropyridin-3-yl)-1-isopropyl-1H-1,2,4-triazole (Compound No. 17)

In 20 ml of dichlorobenzene were dissolved 5.8 g of N-methyl-N-phenylsulfonyl-2-chloro-6-fluorobenzohydrazonoyl chloride and 2.3 g of 6-chloro3-cyanopyridine, to which was added 2.2 g of anhydrous aluminum chloride at room temperature with stirring. The resulting solution was raised to 140° C. in an oil bath and stirred for 30 minutes. After the completion of the reaction, the reaction solution was dissolved with 200 ml of chloroform. The chloroform solution was washed with a diluted alkali solution and further with a diluted hydrochloric acid solution. After the washing with water, the organic layer was dried over anhydrous magnesium sulfate and concentrated under a reduced pressure. The resulting concentrate was subjected to chromatography of silica gel (trade mark: Wakogel C-200) using a mixed solution of hexane and ethyl acetate as a developing solvent to obtain 1.0 g (yield: 18.9%) of a desired brown viscous liquid (refractive index (n$_D$20): measurement impossible).

NMR data (60 MHz, CDCl$_3$ solvent, δ value) 1.60 (d, 6H) 4.45–4.95 (m, 1H) 6.95–7.55 (m, 4H) 7.95 (dd, 1H) 8.65 (d, 1H)

An insecticide contains a triazole derivative represented by the general formula [II] as an active ingredient.

When the triazole compounds formed by using the benzhydrazone derivative according to the invention as an intermediate are used as an active ingredient for insecticides, these compounds themselves may be used alone, or may be compounded with a carrier, a surfactant, a dispersing agent, an adjuvant or the like to form dusts, wettable powder, emulsion, fine powder, granulates or the like. As the carrier used in the formulation of agricultural chemicals, mention may be made of a solid carrier such as zeeklite, talc, bentonite, clay, kaolin, diatomaceous earth, white carbon, vermiculite, calcium hydroxide, quartz sand, ammonium sulfate, urea or the like; and a liquid carrier such as isopropyl alcohol, xylene, cyclohexanone, methylnapthalene or the like. As the surfactant and dispersing agent, mention may be made of a metal salt of alkylbenzene sulfonic acid, a metal salt of dinaphtylmethane disulfonic acid, a sulfuric acid ester of alcohol, alkylarylsulfonate, lignin sulfonate, polyoxyethylene glycol ether, polyoxyethylene alkylaryl ether, polyoxyethylene sorbitan monoalkylate and the like. As the adjuvant, mention may be made of carboxymethylcellulose, polyethylene glycol, gum arabi and the like.

In the formulation, the amount of the active ingredient used may be selected in accordance with the use purpose, but it is properly selected within a range of 0.05–20% by weight, preferably 0.1–10% by weight in case of the dusts and granules. In case of the emulsion and wettable powder, the amount of the active ingredient is properly selected within a range of 0.5–80% by weight, preferably 1–60% by weight.

The insecticide may be used by spraying onto stem and leaves, by applying to soil, by applying to a nursery box, by spraying onto water surface or the like. In use, the insecticide is directly applied or sprayed by diluting to a proper concentration. The amount of the insecticide applied is dependent upon the kind of the compound used as an active ingredient, injurious insect to be controlled, tendency and degree of insect injury, environmental condition, kind of formulation used and the like. When the insecticide is directly used as dusts or granules, the amount of the active ingredient is properly selected within a range of 0.05 g–5 kg, preferably 0.1–1 kg per 10 are. Furthermore, when it is used in form of a liquid as emulsion or wettable powder, the amount of the active ingredient is properly selected within a range of 0.1–5000 ppm, preferably 1–1000 ppm.

Moreover, the insecticide may be used by mixing with other insecticide, fungicide, fertilizer, plant growth regulator and the like.

The formulation will concretely be described with respect to typical examples. In this case, the kind of the compounds and additives and the compounding ratio are not limited to these examples and may be varied within wide ranges. Moreover, % is by weight otherwise specified.

Formulation Example 1

Emulsion

An emulsion was prepared by uniformly dissolving 30% of the compound 12, 20% of cyclohexanone, 11% of polyoxyethylene alkylaryl ether, 4% of calcium alkylbenzene sulfonate and 35% of methylnaphthaline.

Formulation Example 2

Wettable Powder

A wettable powder was prepared by uniformly mixing and pulverizing 40% of the compound 9, 15% of diatomaceous earth, 15% of clay, 25% of white carbon, 2% of sodium dinaphthylmethane disulfonate and 3% of sodium lignin sulfonate.

Formulation Example 3

Dust

A dust was prepared by uniformly mixing and pulverizing 2% of the compound 7, 5% of diatomaceous earth and 93% of clay.

Formulation Example 4

Granule

5% of the compound 13, 2% of sodium salt of lauryl alcohol sulfuric acid ester, 5% of sodium lignin sulfonate, 2% of carboxymethyl cellulose and 86% of clay were uniformly mixed and pulverized. Then, 100 parts by weight of the resulting mixture was added with 20 parts by weight of water and kneaded and shaped into granules of 14–24 mesh through an extrusion type granulating machine and dried to form granules.

The aforementioned triazole derivatives are effective to control aphids such as cotton aphid, green peach aphid, cabbage aphid and the like; planthoppers such as brown planthopper, white-backed planthopper, small brown planthopper and the like; leafhoppers such as green rice leafhopper, tea green leafhopper and the like; whiteflies such as greenhouse whitefly and the like; hemipteran injurious insects such as mulberry scale, corbett rice bug and the like; lepidopteran injurious insects such as diamond-back moth, lima-bean cutworm, tobacco cutworm and the like; dipteran injurious insects such as house fly, mosquito and the like; elytron injurious insects such as rice plant weevil, soy bean weevil, cucurbit leaf beetle and the like; roaches such as American cockroach, steam fly and the like; and mites such as two-spotted spider mite, kanzawa spider mite, citrus red mite and the like.

Especially, the above insecticides show a very excellent effect of controlling aphids such as cotton aphid, green peach aphid, foxglove aphid, cabbage aphid and the like; whiteflies such as greenhouse whitefly, sweet potato whitefly and the like; hemipteran injurious insects such as mulberry scale and the like; thrips such as southern yellow thrip and the like; and mites such as two-spotted spider mite, kanzawa spider mite, citrus red mite and the like.

The effect of the compounds as mentioned above will be described with respect to the following test examples. Moreover, the following compounds were used as a comparative chemical. Comparative chemicals A to C are compounds disclosed in Research Disclosure RD 278004 and are used by the same formulation as described above, while comparative chemicals D and E are commercial products usually used for control of aphids.

Comparative chemical A: 3-(2-chlorophenyl)-5-(2-chloropyridin-3-yl)-1-methyl-1H-1,2,4-triazole Comparative chemical B: 3-(2-chlorophenyl)-5-(6-chloropyridin-3-yl)-1-methyl-1H-1,2,4-triazole Comparative chemical C: 3-(2-chloro-4-fluorophenyl)-5-(6-chloropyridin-3-yl)-1-methyl-1H-1,2,4-triazole Comparative chemical D: 45% wettable powder of Methomyl Comparative chemical E: 50% emulsion of Ethiophencarb Test Example 1

Insecticidal Test through Immersion Process

The wettable powder prepared according to Formulation Example 2 was diluted with water so that the concentration of the active ingredient was 0.8 ppm or 0.16 ppm. In the resulting diluted wettable powder were immersed cucumber seedlings previously inoculated with larvae of cotton aphid and then subjected to a drying treatment in air. After the treatment, the cucumber seedlings were placed in a thermostatic chamber of 25° C. for 3 days and then number of larvae died was counted to calculate the percentage of mortality. The test was carried out by double series. The results are shown in Table 3.

TABLE 3

| Compound No. | Mortality (%) | |
|---|---|---|
| | 0.8 ppm | 0.16 ppm |
| 7 | 100 | 65 |
| 9 | 100 | 60 |
| 12 | 100 | 100 |
| 13 | 100 | 100 |
| Comparative chemical A | 14 | 27 |
| Comparative chemical B | 100 | 35 |
| Comparative chemical C | 61 | 26 |

Test Example 2

Insecticidal Test through Injection Process

The wettable powder prepared according to Formulation Example 2 was diluted with water so that the concentration of the active ingredient was 0.8 ppm or 0.16 ppm. The resulting diluted wettable powder was injected into a pot containing cucumber seedlings previously inoculated with larvae of cotton aphid. After the injection, the cucumber seedlings were placed in a thermostatic chamber of 25° C. for 3 days and then the number of larvae died was counted to calculate the percentage of mortality. The test was carried out by double series. The results are shown in Table 4.

TABLE 4

| Compound No. | Mortality (%) | |
|---|---|---|
| | 0.8 ppm | 0.16 ppm |
| 7 | 100 | 100 |
| 8 | 100 | 65 |
| 9 | 100 | 60 |
| 12 | 100 | 100 |
| 13 | 100 | 100 |
| Comparative chemical A | 85 | 0 |
| Comparative chemical B | 80 | 40 |
| Comparative chemical C | 65 | 35 |

Test Example 3

Test for Systemic Translocation Control through Soil Improving Treatment Process Granules prepared according to Formulation Example 4 (0.5 kg per 10 are) were applied to stub roots of cucumber seedlings platted in a pot and previously inoculated with aphid larvae. After the treatment, the pot was placed in a green house, during which the number of living adults and larvae was counted every 7 days. The test was carried out by triple series. The results are shown in Table 5.

TABLE 5

| Compound No. | Number of living adults and larvae | | |
|---|---|---|---|
| | before treatment | days after treatment | |
| | | 7 days | 14 days |
| 13 | 40 | 5 | 0 |
| Comparative chemical A | 35 | 89 | 27 |
| Comparative chemical B | 40 | 321 | 433 |
| Comparative chemical D | 39 | 26 | 108 |
| non-treated | 32 | 427 | 392 |

Test Example 4

Test for Systemic Translocation Control through Spraying Process on Stem and Leaves The wettable powder prepared according to Formulation Example 2 was diluted with water so that the concentration of the active ingredient was 100 ppm. The resulting diluted wettable powder was sprayed onto only front sides of leaves in cucumber seedlings platted in a pot and previously inoculated at their back sides with aphid larvae without being sprayed onto the back sides. After the treatment, the pot was placed in a green house, during which the number of adults and larvae living in the back sides was counted every 5 days. The test was carried out by triple series. The results are shown in Table 6.

TABLE 6

| Compound No. | Number of living adults and larvae | | | |
|---|---|---|---|---|
| | before treatment | days after treatment | | |
| | | 5 days | 10 days | 15 days |
| 13 | 31 | 0 | 6 | 8 |
| Comparative chemical A | 32 | 50 | 327 | 283 |
| Comparative chemical B | 29 | 4 | 10 | 71 |
| Comparative chemical E | 32 | 95 | 420 | 289 |
| non-treated | 32 | 151 | 323 | 128 |

What is claimed is:

1. A benzhydrazone compound having the following formula I:

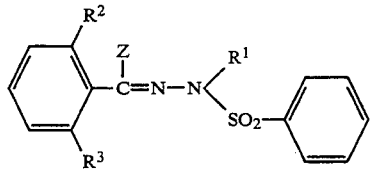

wherein $R^1$ is a lower alkyl group, $R^2$ and $R^3$ are same or different halogen atoms and Z is a chlorine atom or an amino group.

2. A benzhydrazone compound according to claim 1, wherein said $R^1$ in the formula I is a methyl group, $R^2$ and $R^3$ are fluorine atom or chlorine atom and Z is a chlorine atom.

3. A benzhydrazone compound according to claim 1, wherein said $R^1$ in the formula I is a methyl group, $R^2$ and $R^3$ are fluorine atom or chlorine atom and Z is an amino group.

* * * * *